(12) United States Patent
Alam et al.

(10) Patent No.: US 9,194,805 B2
(45) Date of Patent: Nov. 24, 2015

(54) TRACE DETECTION OF ANALYTES USING PORTABLE RAMAN SYSTEMS

(71) Applicant: Sandia Corporation, Albuquerque, NM (US)

(72) Inventors: M. Kathleen Alam, Cedar Crest, NM (US); Peter J. Hotchkiss, Albuquerque, NM (US); Laura E. Martin, Edgewood, NM (US); David Alexander Jones, Sandia Park, NM (US)

(73) Assignee: Sandia Corporation, Albuquerque, NM (US)

( * ) Notice: Subject to any disclaimer, the term of this patent is extended or adjusted under 35 U.S.C. 154(b) by 0 days.

(21) Appl. No.: 14/469,933

(22) Filed: Aug. 27, 2014

(65) Prior Publication Data

US 2015/0062576 A1    Mar. 5, 2015

Related U.S. Application Data

(60) Provisional application No. 61/870,496, filed on Aug. 27, 2013.

(51) Int. Cl.
*G01J 3/44* (2006.01)
*G01N 21/65* (2006.01)
*G01J 3/02* (2006.01)

(52) U.S. Cl.
CPC ............... *G01N 21/658* (2013.01); *G01J 3/02* (2013.01); *G01N 21/65* (2013.01)

(58) Field of Classification Search
CPC .............. G01J 3/02; G01J 3/44; G01N 21/65; G01N 21/658; G01N 2021/656
USPC .............................................. 356/301, 72–73
See application file for complete search history.

(56) References Cited

U.S. PATENT DOCUMENTS

| | | | |
|---|---|---|---|
| 7,876,425 B2 | 1/2011 | Sardashti et al. | |
| 8,022,360 B2 | 9/2011 | Taylor | |
| 8,432,544 B2 | 4/2013 | Yao et al. | |
| 8,587,787 B2 | 11/2013 | Reyes et al. | |
| 8,652,632 B2 | 2/2014 | Demirel et al. | |
| 8,734,722 B2 | 5/2014 | Taylor | |
| 8,771,613 B2 | 7/2014 | Martin et al. | |
| 2013/0038869 A1* | 2/2013 | Lascola et al. | ................ 356/301 |

* cited by examiner

*Primary Examiner* — Abdullahi Nur
(74) *Attorney, Agent, or Firm* — Michael A. Beckett

(57) ABSTRACT

Apparatuses and methods for in situ detection of a trace amount of an analyte are disclosed herein. In a general embodiment, the present disclosure provides a surface-enhanced Raman spectroscopy (SERS) insert including a passageway therethrough, where the passageway has a SERS surface positioned therein. The SERS surface is configured to adsorb molecules of an analyte of interest. A concentrated sample is caused to flow over the SERS surface. The SERS insert is then provided to a portable Raman spectroscopy system, where it is analyzed for the analyte of interest.

14 Claims, 13 Drawing Sheets

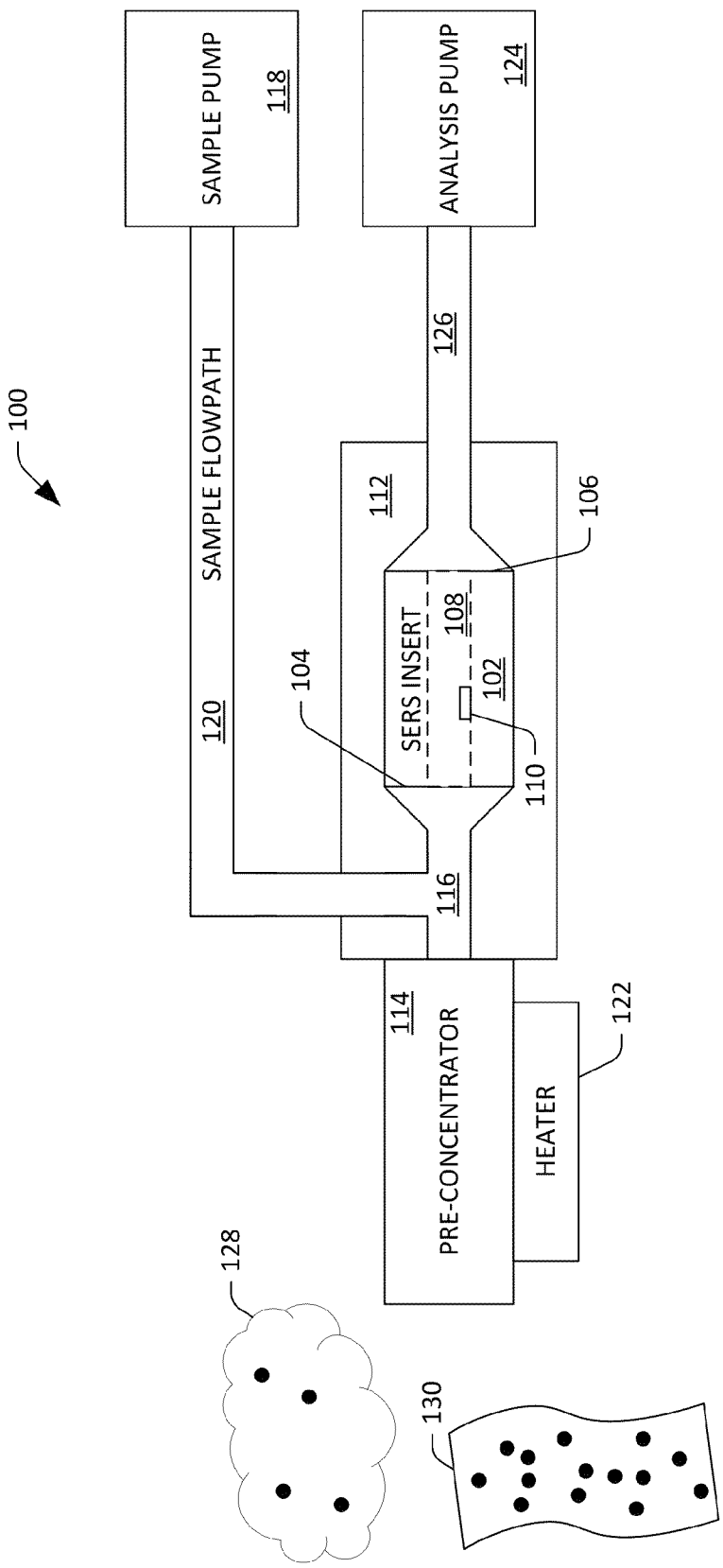

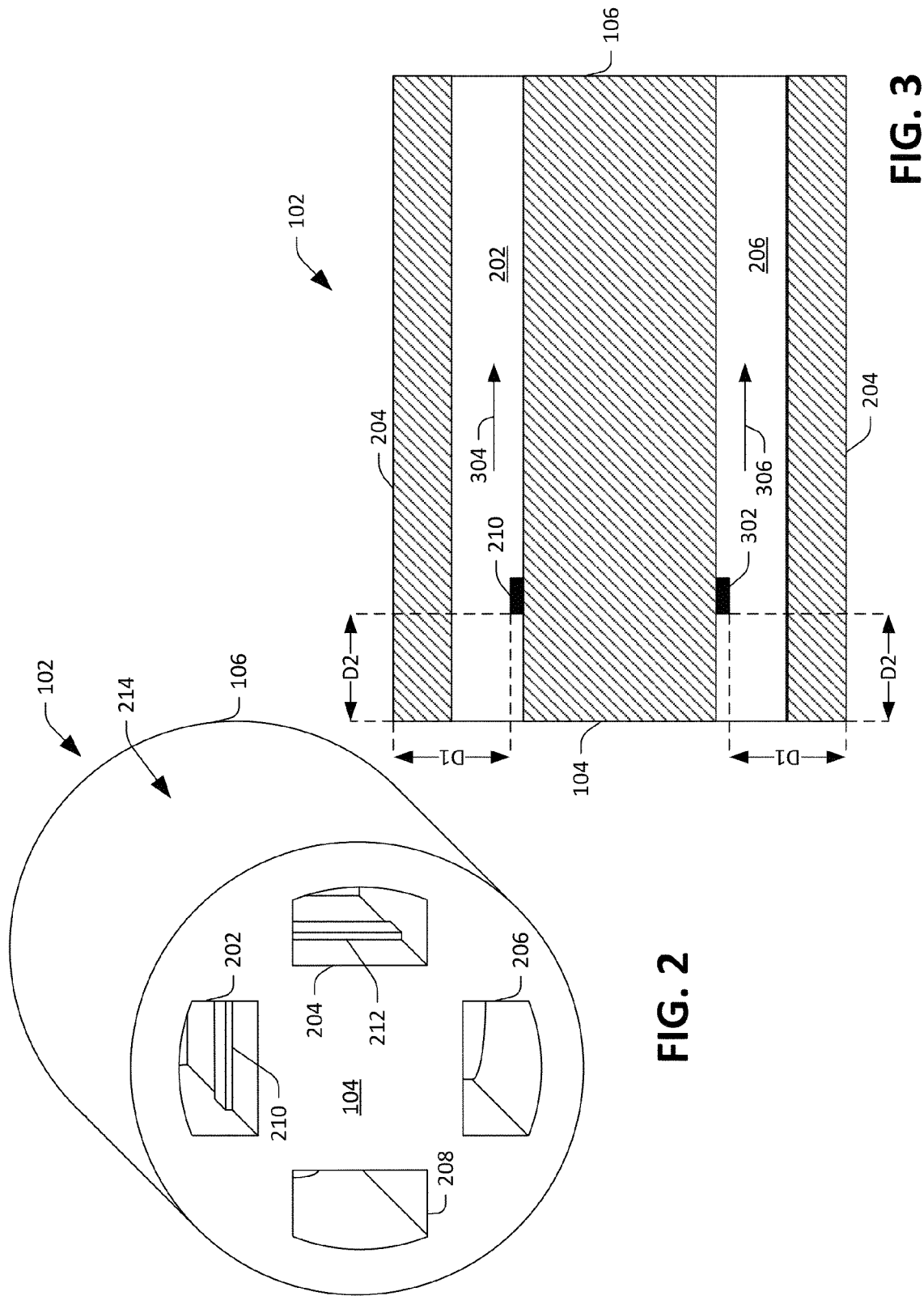

TRACE DETECTION OF ANALYTES USING PORTABLE RAMAN SYSTEMS

RELATED APPLICATION

This application claims priority to U.S. Provisional Patent Application No. 61/870,496, filed on Aug. 27, 2013, and entitled "SERS SAMPLING METHODS FOR HAND-HELD PORTABLE RAMAN", the entirety of which is incorporated herein by reference.

STATEMENT OF GOVERNMENTAL INTEREST

This invention was developed under Contract DE-AC04-94AL85000 between Sandia Corporation and the U.S. Department of Energy. The U.S. Government has certain rights in this invention.

BACKGROUND

Portable Raman systems are used in the field by a variety of personnel (e.g., military, civilian safety, homeland security, etc.) to identify or detect a material of interest. Portable Raman systems, however, are often limited by proximity to an object that is to be analyzed. Additionally, portable Raman systems are limited in sensitivity.

In an operation of a portable Raman system, a liquid or solid sample is acquired or formed and placed in a vial. The vial, in turn, is positioned relative to a laser of the portable Raman system, which directs laser light towards the sample in the vial. Summarily, a detector can detect backscattered radiation from the point of illumination of the laser, and features of the backscattered radiation are indicative of a type of molecule in the sample. Again, however, portable Raman systems are sometimes unable to perform all functions desired by an end user, due to the limitations of conventional Raman systems referenced above.

SUMMARY

The present disclosure provides apparatuses and methods for in situ trace detection of an analyte. In a general embodiment, the present disclosure provides an apparatus that facilitates performance of trace detection of at least one analyte. The apparatus comprises a surface enhanced Raman spectroscopy (SERS) insert. The SERS insert comprises a proximal end, a distal end, a plurality of passageways that extend laterally through the SERS insert from the proximal end to the distal end, and a plurality of SERS surfaces that are respectively positioned in the passageways. Each of the SERS surfaces is configured to attract molecules of the at least one analyte. The SERS insert is configured for insertion into a handheld Raman spectroscopy system.

Generally, the SERS insert can be configured for use with conventional portable Raman spectroscopy systems (Raman systems). Thus, the SERS insert has a size and shape that accord to vials used in conventional portable Raman systems. The SERS insert includes at least one passageway (e.g., channel) that extends laterally through the SERS insert. A SERS surface is positioned in the passageway of the SERS insert, where the SERS surface is composed of a metal, such as gold or silver, and is (optionally) functionalized to attract molecules of an analyte of interest. For instance, the SERS surface can be functionalized to attract molecules of an explosive, such as trinitrotoluene (TNT). In another example, a SERS surface need not be functionalized, but nevertheless attracts molecules of an analyte of interest. A position of the SERS surface in the passageway is selected such that a focal point of a laser beam emitted by a laser in the portable Raman system is on the SERS surface.

To allow for performance of trace detection, a concentrated sample is directed through the passageway of the SERS insert prior to the SERS insert being provided to the portable Raman system. A system is described herein that is configured to acquire the concentrated sample and subsequently direct the concentrated sample through the passageway of the SERS insert, wherein the SERS surface of the SERS insert attracts molecules of an analyte of interest that exist in the concentrated sample. The above mentioned system includes a receiving region that is configured to receive the SERS insert and mechanically stabilize the SERS insert relative to the remainder of the system. When positioned in the receiving region, the SERS insert is placed in fluid communication with an inlet flowpath and an outlet flowpath, where the concentrated sample is introduced to the SERS insert by way of the inlet flowpath and exits the SERS insert by way of the outlet flowpath.

Described briefly, in operation, the system is configured to acquire the concentrated sample, and thereafter cause the concentrated sample to flow through the passageway of the SERS insert; entering the passageway at the inlet flowpath and exiting the passageway at the outlet flowpath. When the concentrated sample includes molecules of the analyte of interest, at least some of such molecules will be attracted to the SERS surface positioned in the passageway of the SERS insert. Because the sample is concentrated (e.g., the parts per million (ppm) of the molecule will be increased relative to a sample upon which the concentrated sample is based), when the analyte is present in the sample, there will be a sufficient volume of molecules of the analyte in the concentrated sample to allow for detection of the analyte when the SERS surface is interrogated by way of a portable Raman system. Once the concentrated sample has been directed through the passageway of the SERS insert, the SERS insert can be removed from the system and provided to the portable Raman system.

Additional features and advantages are described herein, and will be apparent from the following Detailed Description and the figures.

BRIEF DESCRIPTION OF THE DRAWINGS

FIG. 1 is a functional block diagram of an exemplary system that facilitates introduction of a concentrated sample to a surface-enhanced Raman spectroscopy (SERS) surface in a SERS insert, the SERS insert configured for use with a portable Raman spectroscopy system (Raman system).

FIG. 2 is an isometric view of an exemplary SERS insert.

FIG. 3 is a cross-sectional view of the exemplary SERS insert.

DETAILED DESCRIPTION

Figure 4:
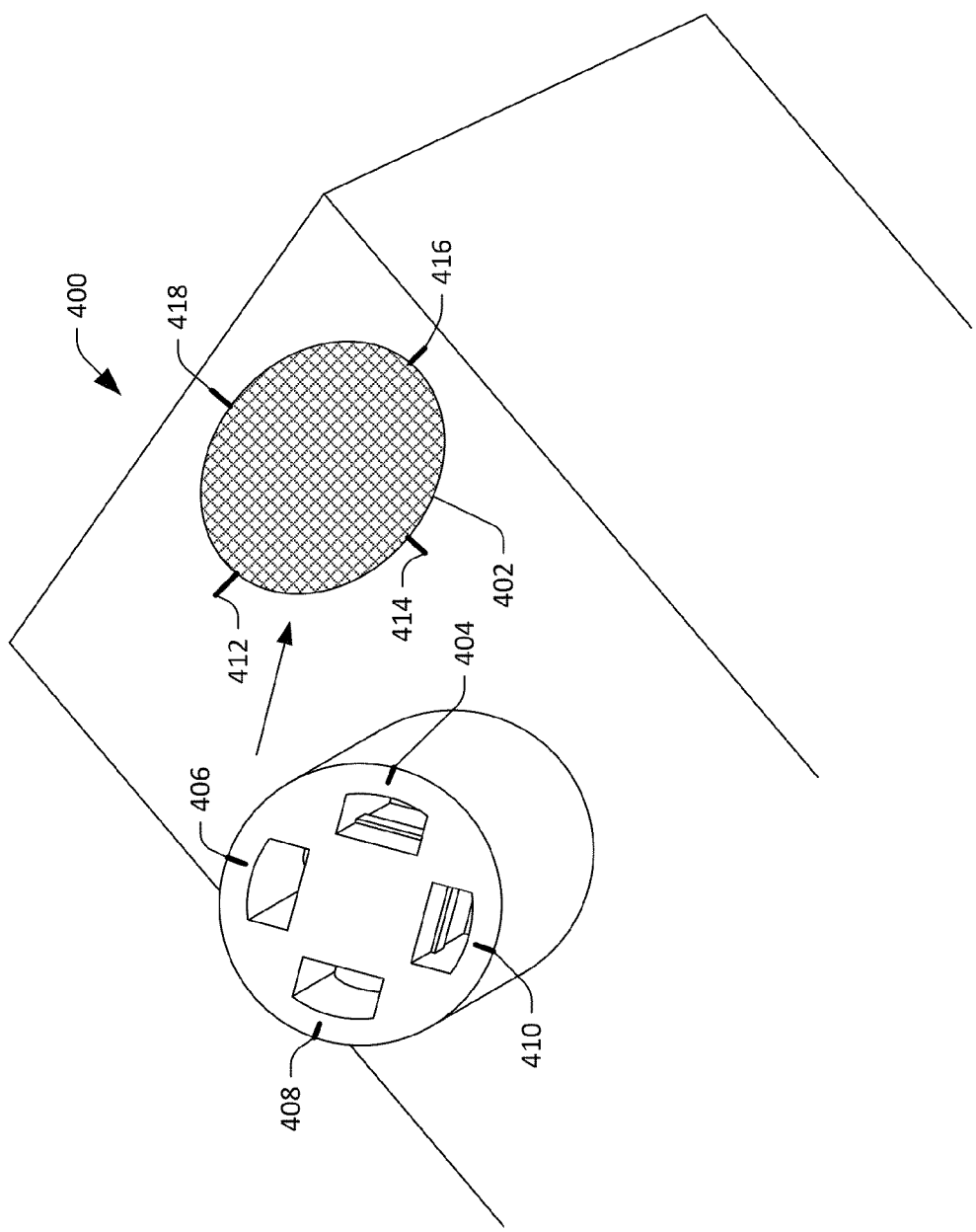
FIG. 4 is an isometric view of the SERS insert being introduced to a portable Raman system.

Apparatuses and methods for in situ trace detection of an analyte are disclosed herein. Generally, technologies pertaining to surface-enhanced Raman spectroscopy (SERS) are leveraged to enable trace detection of the analyte, where advantageous properties of SERS are leveraged to enable such trace detection. The SERS effect is produced when the electric field of an analyte interacts with the electric field of a surface upon which the analyte is located. Typically, the surface is a roughened metal surface that results in an increase in a Raman signal of up to 10 orders of magnitude. Applications of the technologies described herein include, but are not limited to, detection (in situ detection) of contraband materials, such as explosives, illicit drugs, etc., in situ detection of environmental pollutants, amongst other applications.

With reference now to FIG. 1, in an embodiment, a system 100 that facilitates in situ trace detection of an analyte is illustrated. As will be described in greater detail herein, surface-enhanced Raman spectroscopy (SERS) is leveraged to facilitate such in situ trace detection of the analyte, where a concentrated volume of the analyte is provided to a SERS surface, and advantageous features of SERS are leveraged to perform the above-referenced trace detection. The system 100 comprises a SERS insert 102. The SERS insert 102 can be composed of a transparent material, such as glass, a plastic, or the like. The SERS insert 102 can have a shape that conforms to a conventional portable Raman spectroscopy system (Raman system). For instance, the SERS insert 102 may be cylindrical, such that it mimics the shape of a vial that is typically used in conventional portable Raman systems. In other examples, the shape of the SERS insert 102 may be cubicle, an ellipsoid, or the like.

The SERS insert 102 has a proximal end 104 and a distal end 106, wherein the proximal end 104 and the distal and 106 define a lateral length of the SERS insert 102. The SERS insert 102 further includes at least one passageway 108 (e.g., channel) that extends laterally through the SERS insert 102 between the proximal end 104 and the distal end 106. The SERS insert 102 further comprises an SERS surface 110 that is positioned in the passageway 108. The SERS surface 110 can be composed of a suitable metal, such as gold or silver, where the surface of such metal is roughened to enhance a Raman signal with respect to an analyte of interest. As will be described in greater detail below, the SERS surface 110 can facilitate: 1) attraction between the SERS surface 110 and molecules of the analyte of interest; and 2) enhancement of a Raman signal when the SERS surface 110 is interrogated by a laser of a portable Raman system. In an example, the SERS surface 110 can be functionalized to facilitate the attraction and enhancement referenced above. In another example, the SERS surface 110 need not be functionalized—instead, the SERS surface 110 can be non-functionalized roughened or patterned metal. Exemplary analytes include, but are not limited to, contraband materials, such as explosives, illicit drugs, etc., environmental pollutants, and the like. In a particular example, the SERS surface 110 can be modified using thiol chemistry, which can facilitate enhanced detection of TNT vapors when a portable Raman system interrogates the SERS surface 110.

As can be ascertained, even when a volume of air includes an analyte, to detect such analyte in the volume of air, a sufficient volume of molecules of the analyte must be introduced to the SERS surface 110. The system 100 is configured to acquire a concentrated sample and introduce the concentrated sample to the SERS surface 110 by way of the passageway 108 in the SERS insert 102. Therefore, when traces of the analyte of interest are existent in a region being monitored (e.g., in the air), then the concentrated sample will have a sufficient volume of molecules of the analyte to allow for trace detection of the analyte when the SERS surface 110 is interrogated with a laser of a portable Raman system. Conversely, when traces of the analyte are not existent in the region being monitored, the concentrated sample will fail to include molecules of the analyte, and therefore interrogation of the SERS surface will result in a determination that the region being monitored fails to include the analyte.

The system 100 additionally includes a receiving system 112 that is configured to mechanically secure (stabilize) the SERS insert 102 in an appropriate position in the system 100. For example, the receiving system 112 may include notches, clasps, or the like, that when interfaced with the SERS insert 102, cause the SERS insert 102 to be mechanically stabilized in the receiving system 112.

The system 100 also comprises a pre-concentrator 114 and an inlet flowpath 116, wherein the SERS insert 102 is in fluid communication with the pre-concentrator 114 by way of the inlet flowpath 116. More specifically, the inlet flowpath 116 fluidically couples the pre-concentrator 114 with the passageway 108 of the SERS insert 102 at the proximal end 104 of the SERS insert 102. The system 100 also includes a sample pump 118 and a sample flowpath 120, wherein the pre-concentrator 114 and the sample pump 118 are in fluid communication by way of the sample flowpath 120. As shown, in an example, the sample flowpath 120 and the inlet flowpath 116 may intersect between the pre-concentrator 114 and the SERS insert 102.

The system 100 also comprises a heater 122 that is positioned relative to the pre-concentrator 114, such that heat generated by the heater 122 can be transferred to the pre-concentrator 114 (e.g., heat can be transferred to an internal chamber of the pre-concentrator 114). The heater 122 may be a resistive heater or other suitable heater.

The system 100 also comprises an analysis pump 124 and an outlet flowpath 126, wherein the outlet flowpath 126 fluidically couples the passageway 108 of the SERS insert 102 with the analysis pump 124 at the distal end 106 of the SERS insert 102. As will be described below, in some embodiments, one or more of the pre-concentrator 114, heater 122, sampling pump 118, and/or sample flowpath 120 are not included in the system 100.

Operation of the system 100 will now be described. The system 100 is placed in a region where, for example, one of a sample of air 128 or a sample from a material 130 is to be analyzed for existence of an analyte. The material may be, for instance, a cloth, a swab, a metal mesh, plastic, a cotton wipe, or any other suitable medium. With respect to the material 130, such cloth may have been wiped across another material, such as an article of clothing, a piece of baggage, etc., to acquire a sample.

As shown by the circles in the air 128, such air 128 may include trace amounts of the analyte of interest. The sampling pump 118 is activated, causing the air 128 to be directed through a chamber in the pre-concentrator 114 at a predefined flow rate. For instance, while not shown, the pre-concentrator 114 may include a passageway therethrough, such that when the sampling pump 118 is activated, air flows through the chamber of the pre-concentrator 114. The pre-concentrator 114 includes a sorbent material that is configured to absorb of adsorb molecules of the analyte that is to be detected. Thus, as the air 128 flows through the pre-concentrator 114 (e.g., and through the sample path 120 until it exits the system 100), molecules of the analyte are absorbed or adsorbed by the sorbent material in the chamber of the pre-concentrator 114. After the sampling pump 118 has been operated for some suitable amount of time, the heater 122 is activated to heat the sorbent material of the pre-concentrator 114. This causes molecules of the analyte to desorb from the sorbent material, resulting in formation of a concentrated sample, where the parts per million (ppm) of the molecule in the concentrated sample is greater than the ppm of the molecule in the air 128.

Responsive to the molecules of the analyte being desorbed in the chamber of the pre-concentrator 114, the analysis pump 124 can be activated. This causes the concentrated sample to (relatively slowly) flow from the chamber of the pre-concentrator 114, through the inlet flowpath 116, through the passageway 108 of the SERS insert 102, and through the outlet flowpath 126. At least some molecules of the analyte are attracted to the SERS surface 110 as the molecules flow through the passageway 108 of the SERS insert 102. Because the concentrated sample has an enhanced concentration of molecules of the analyte relative to the air 128 in the region proximate to the system 100, a sufficient volume of such molecules may adsorb to the SERS surface 110 to allow a portable Raman system to detect existence of the molecules of the analyte on the SERS surface 110, and thus existence of trace elements of the analyte in the air 128.

When the sample to be tested is the material 130, the material 130 may already have a suitable concentration of molecules of the analyte thereon. Accordingly, the system 100 may not include the sample pump 118, the sample flowpath 120, the pre-concentrator 114, or the heater 122. Instead, the material 130 can be positioned in fluid communication with the SERS surface 110 by way of the inlet flowpath 116 and the passageway 108 of the SERS insert 102 (e.g., the material 130 can be placed next to a nozzle that is fluidically coupled to the inlet flowpath 116). The analysis pump 124 can be activated, which can cause molecules of the analyte to be released from the material 130 and flow through the passageway 108 (in close proximity to the SERS surface 110). As described above, the molecules of the analyte can adsorb to the SERS surface 110, wherein when there is a sufficient volume of molecules of the analyte on the material 130, a sufficient volume of such molecules will adsorb to the SERS surface 110 to allow for trace detection of the analyte on the material 130 by way of a portable Raman system.

Now referring to FIG. 2, an isometric view of the exemplary SERS insert 102 is illustrated. While the shape of the SERS insert 102 is illustrated in FIG. 2 as being cylindrical, as mentioned previously, the SERS insert 102 may be any suitable shape (so long as it can be received by a portable Raman system). In the example shown here, the SERS insert 102 comprises a plurality of passageways 202-208 (e.g. 4 passageways) that extend laterally through the SERS insert 102. Each of the passageways 202-208 has a respective SERS surface positioned therein. For example, the first passageway 202 has a first SERS surface 210 positioned therein, the second passageway 204 has a second SERS surface 212 positioned therein, the third passageway 206 has a third SERS surface (not shown) positioned therein, and the fourth passageway 208 has a fourth SERS surface (not shown) positioned therein. While the SERS insert 102 is shown as including four passageways 202-208, it is to be understood that the SERS insert 102 can include more (e.g., up to 10) or fewer (as few as one) passageways. In a particular example, a number of passageways in the SERS insert 102 can be between two passageways and four passageways.

As can be ascertained, each of the passageways 202-208 extend in parallel with one another, and in parallel with an axis of the SERS insert 102. The passageways 202-208 are defined by respective planar inner surfaces and respective outer surfaces, where the planar inner surfaces are located between the central axis of the SERS insert 102 and an outer surface 214 of the SERS insert 102. Further, the SERS surfaces 210-212 are aligned with one another in a cross section of the SERS insert 102, such that they are collectively positioned equidistantly from the proximal end 104 (and the distal end 106) of the SERS insert 102.

Still further, the SERS surfaces 210-212 positioned in the passageways 202-208 may be positionally biased along the axis of the SERS insert 102 towards the proximal end 104 of the SERS insert 102 relative to the distal end 106 (e.g., the SERS surfaces 210-212 may be closer to the proximal end 104 than they are to the distal end 106 of the SERS insert 102). This is because conventional portable Raman systems are configured to analyze solid or liquid samples in a vial, where a laser of the portable Raman system is focused near the bottom of the vial, such that a large volume of the solid or liquid need not be acquired to be analyzed by the portable Raman system. To avoid requiring reconfiguration of a portable Raman system, the SERS surfaces 210-212 are positioned in accord with the conventional focal point of a laser beam emitted by the laser of the portable Raman system.

Still further, the SERS surfaces 210-212 in the passageways 202-208 are precisely positioned relative to the outer surface 214 of the SERS insert 102. The reasoning for such precision is due to conventional operating parameters of portable Raman systems. As noted above, lasers used in such systems are configured to emit laser beams with focal points at a particular depth in a vial. The SERS surfaces 210-212 are positioned relative to the outer surface 214 of the SERS insert 102 in accordance with the aforementioned depth.

There are several advantages with respect to having multiple passageways through the SERS insert 102 (with respective multiple SERS surfaces positioned therein). A first advantage pertains to redundancy—when the concentrated sample is directed to flow through each of the passageways 202-208, each of the respective SERS surfaces will have been exposed to the concentrated sample, and molecules can adsorb to each of the SERS surfaces. Thereafter, the portable Raman system can be configured to analyze each SERS surface in the SERS insert 102. Obtaining more than one measurement with respect to the concentrated sample can reduce occurrences of false positives and/or can increase confidence as to whether a region does or does not include traces of the analyte.

In another example, SERS surfaces can be chemically derivatized (functionalized) with respect to different analytes. Thus, the SERS insert 102 can have different SERS surfaces functionalized differently (e.g., for different analytes). Further, the SERS surfaces in the SERS insert 102 may include one or more non-functionalized SERS surfaces. Specifically, an issue with Raman spectroscopy systems is that if more than one type of molecule is existent in a sample when a portable Raman spectroscopy system analyzes the sample, a combined spectrum may be output by the Raman spectroscopy system. This combined spectrum can be difficult to interpret. By having multiple SERS surfaces configured to attract different molecule types, a single SERS insert 102 can allow for relatively specific analysis of different analytes. This can reduce confusions, false positives, etc.

Returning to FIG. 1, an exemplary operation of the system 100 when the SERS insert 102 includes multiple passageways with different respective SERS surfaces positioned therein is described. Initially, it may be desired to cause the first SERS surface 210 positioned in the first passageway 202 to be exposed to molecules of an analyte (if existent in a concentrated sample), wherein the first SERS surface 210 is configured specifically for the analyte. When the first SERS surface 210 is to be exposed to molecules of the analyte, other passageways in the SERS insert 102 can be blocked (e.g., the passageways 204-208 can be blocked), such that airflow through such passages is prevented.

Before or after blockage of the passageways, the sample pump 118 can be activated, wherein various molecules of various analytes may be absorbed in the sorbent material of the pre-concentrator 114 or adsorb to the sorbent material of the pre-concentrator. The sample pump 118 may then be stopped, and the heater 122 can be configured to heat the sorbent material to a particular temperature, wherein such temperature causes molecules of a first analyte to desorb from the sorbent material of the pre-concentrator 114. The first SERS surface 210 in the (unblocked) first passageway 202 can attract molecules of the first analyte. Thereafter, the analysis pump 124 can be activated, causing the concentrated sample (which includes a concentrated volume of the molecules of the first analyte) to flow through the first passageway 202 over the SERS surface 210 that attracts molecules of the first analyte. The analysis pump 124 may then be stopped.

Thereafter, the first passageway 202 can be blocked (preventing further airflow therethrough), and the second passageway 204 in the SERS insert 102 can be unblocked. The heater 122 may then be operated to further increase the temperature of the sorbent material, such that molecules of a second analyte are desorbed from the sorbent material of the pre-concentrator 114. In another embodiment, the sample pump 118 can be operated again to acquire more air into the pre-concentrator prior to the heater 122 further increasing the temperature of the sorbent material. The second SERS surface 212 in the second passageway 204 is configured particularly for the second analyte. Responsive to the heater 122 increasing the temperature of the sorbent material in the pre-concentrator, such that molecules of the second analyte are desorbed, the analysis pump 124 can be activated, thereby causing a concentrated sample (concentrated for molecules of the second analyte) to flow through the second passageway 204 (but not through the blocked passageways) and in proximity to the second SERS surface 212. Molecules of the second analyte may adhere to the second SERS surface 212 positioned in the second passageway 204. This process of creating a concentrated sample for a particular analyte and directing the concentrated sample through an appropriate passageway of a SERS insert (such that a SERS surface configured for the analyte is exposed to the concentrated sample) can be repeated for multiple analytes (and thus multiple SERS surfaces).

Now referring to FIG. 3, a cross-sectional view of the SERS insert 102 is illustrated. The cross-sectional view of the SERS insert 102 depicts the first passageway 202 and the third passageway 206 extending through the SERS insert 102 from the proximal end 104 to the distal end 106 of the SERS insert 102. As described previously, the first SERS surface 210 is positioned in the first passageway 202, and a third SERS surface 302 is positioned in the third passageway 206. When the analysis pump 124 is activated, air flows in the direction of arrows 304 and 306 through the passageways 202 and 206 (and the passageways 204 and 208). A face of each of the SERS surfaces 210 and 302 is positioned at a distance D1 from the outer surface 214 of the SERS insert 102. Similarly, a front end of each of the SERS surfaces 210 and 302 is positioned at a distance of D2 from the proximal end 104 of the SERS insert 102. D1 and D2 can be selected based upon operating parameters of a portable Raman system that is to receive the SERS insert 102.

Now referring to FIG. 4, an exemplary portable Raman system 400 is illustrated. The portable Raman system 400 includes a recess 402 that is configured to receive, for example, a vial. As the SERS insert 102 is cylindrical, it has the shape of the vial and, therefore, is configured to be received in the recess 402 of the portable Raman system 400. In an example, the SERS insert 102 may have markings 404-410 thereon, and the portable Raman system 400 may have corresponding markings 412-418 thereon around the recess 402, such that the SERS insert 102 can be properly aligned when positioned in the recess 402 of the portable Raman spectroscopy system 400. For instance, when the markings 404-410 and the markings 412-418 are aligned, a laser in the portable Raman spectroscopy system 400 may be directed at one of the SERS surfaces of the SERS insert 102 (e.g., the laser may be properly aligned). The SERS insert 102 may then be rotated in the recess 402 to allow for analysis of multiple SERS surfaces. In other examples, the recess 402 and/or the SERS insert 102 may have mechanical stops associated therewith, such that it is relatively easy to mechanically align the SERS surfaces with respect to the laser of the portable Raman system 400. In still yet another example, the recess 402 and/or the SERS insert 102 can have magnets appended thereto, such that is relatively easy for a user to mechanically properly align the SERS insert 102 in the recess 402.

Figure 5:
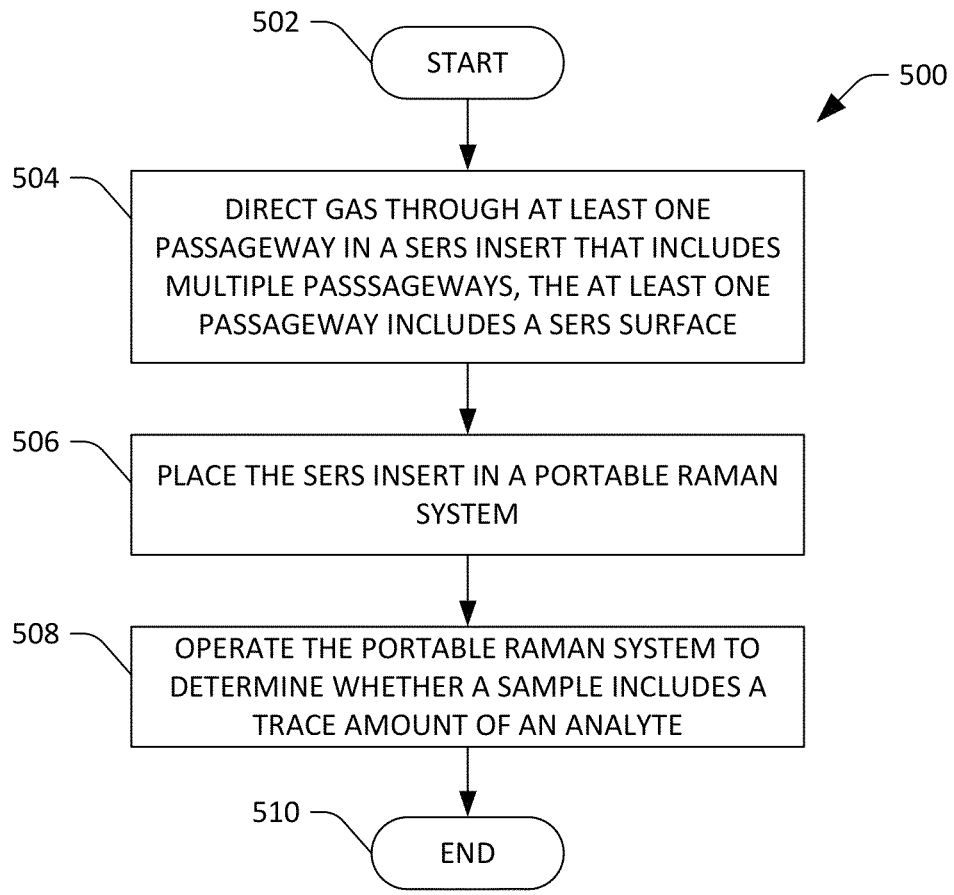
FIG. 5 is a flow diagram that illustrates an exemplary methodology for performing in situ trace detection of an analyte.
Figure 6:
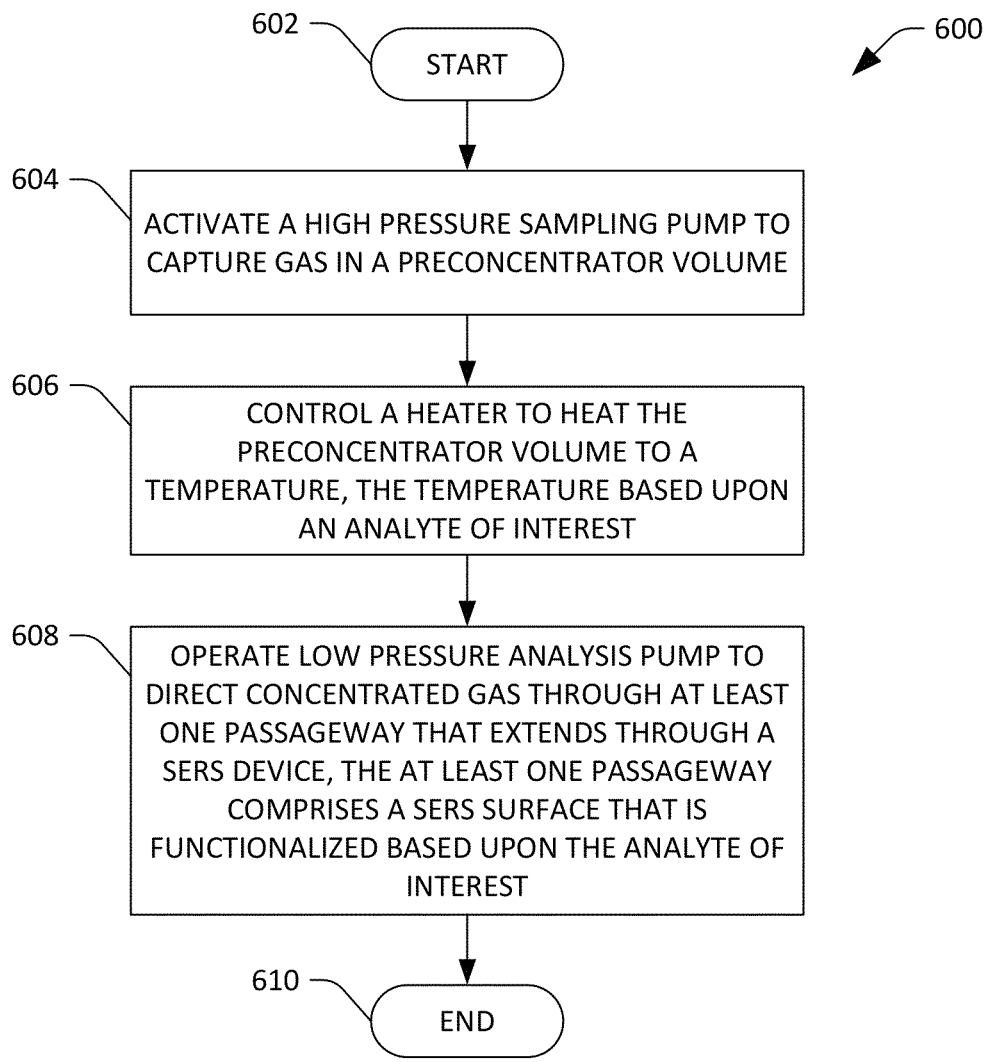
FIG. 6 is a flow diagram that illustrates an exemplary methodology for introducing a concentrated sample in gaseous phase to SERS surface in a SERS insert.
Figure 7:
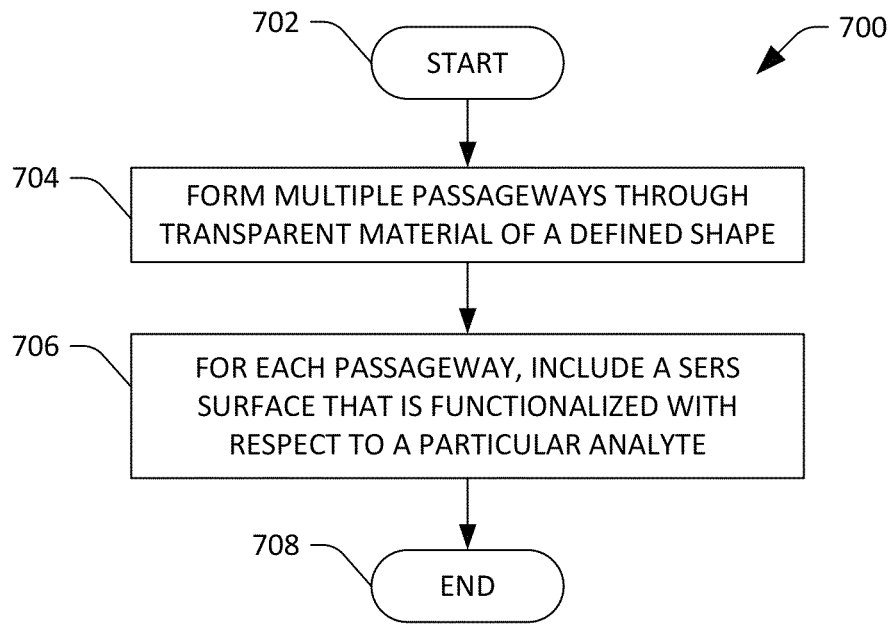
FIG. 7 is a flow diagram that illustrates an exemplary methodology of forming a SERS insert.

FIGS. 5-7 illustrate exemplary methodologies relating to in situ detection of trace amounts of analytes. While the methodologies are shown and described as being a series of acts that are performed in a sequence, it is to be understood and appreciated that the methodologies are not limited by the order of the sequence. For example, some acts can occur in a different order than what is described herein. In addition, an act can occur concurrently with another act. Further, in some instances, not all acts may be required to implement a methodology described herein.

Moreover, the acts described herein may be computer-executable instructions that can be implemented by one or more processors and/or stored on a computer-readable medium or media. The computer-executable instructions can include a routine, a sub-routine, programs, a thread of execution, and/or the like. Still further, results of acts of the methodologies can be stored in a computer-readable medium, displayed on a display device, and/or the like.

Now referring to FIG. 5, an exemplary methodology 500 that facilitates detecting a trace amount of an analyte through utilization of a portable Raman system is illustrated. The methodology 500 starts at 502, and at 504, a gas is directed through at least one passageway in an SERS insert that includes multiple passageways. As described previously, the analysis pump 124 can be activated to cause a concentrated sample to flow through the at least one passageway. Further, as mentioned above, a SERS surface is positioned in the at least one passageway, where, for example, the SERS surface can (optionally) be functionalized in accordance with a particular analyte of interest. Thus, molecules of the analyte of interest adsorb to the SERS surface.

At 506, the SERS insert is placed in a recess of a portable Raman system. This is analogous to a vial that includes a solid or liquid being placed in the recess of the portable Raman spectroscopy system.

At 508, the portable Raman spectroscopy system is operated to cause a signal to be output that is indicative of whether a trace amount of the analyte of interest exists in a sample. As described previously, the sample may be air in a particular region, a material, etc. The methodology 500 completes at 510.

Now referring to FIG. 6, an exemplary methodology 600 that facilitates introducing a concentrated sample to a SERS surface is illustrated. The methodology 600 starts at 602, and at 604, a high-pressure sampling pump is activated to cause air to flow through a chamber in a pre-concentrator that comprises a sorbent material. In an example, the sampling pump can be operated for some threshold amount of time, such as on the order of between 5 seconds and 10 seconds.

At 606, a heater is controlled to heat the sorbent material in the pre-concentrator to a particular temperature, wherein such temperature can cause molecules of an analyte of interest (an analyte that is to be detected) to desorb from the sorbent material. This results in creation of a concentrated sample.

At 608, a low-pressure analysis pump is operated to cause the concentrated sample to flow through at least one passageway of a SERS insert. As described previously, the at least one passageway includes a SERS surface that adsorbs molecules of the analyte. Thus, molecules of the analyte will adhere to the SERS surface. As described previously, at least acts 606 and 608 can be repeated (with the heater operating at different temperatures) to allow for concentrated samples of different molecules to be generated and exposed to different SERS surfaces of the SERS insert. The methodology 600 completes at 610.

Now referring to FIG. 7, an exemplary methodology 700 that facilitates forming a SERS insert is illustrated. The methodology 700 starts at 702, and at 704, multiple passageways are formed through a transparent material of a predefined shape. As noted above, in an example, such shape may be cylindrical. At 706, for each passageway, a respective SERS surface is positioned therein, wherein each SERS surface is respectively configured to attract molecules of a respective analyte. In an example, one or more of the SERS surfaces may be functionalized with respect to one or more analytes. For instance, the SERS surfaces may be functionalized with respect to the same analyte. In another example, the SERS services may be functionalized with respect to different analytes. The methodology 700 completes at 708.

EXAMPLES

By way of example and not limitation, the following examples are illustrative of various embodiments of the present disclosure.

The feasibility of performing SERS with a portable Raman system has been verified using the Thermo Scientific First Defender RM (Ahura). The SERS enhancement of signals from benzoic acid, and representative target materials, ammonium nitrate and TNT, have been demonstrated using: 1) a laboratory instrument and commercial SERS surfaces silver-impregnated sol-gel vials from RealTime Analyzers; and 2) patterned SERS slides from D3 Technologies (Klarite). Both technologies use small metal particles for providing the SERS effect. Klarite relies on gold-coated patterned silicon to provide a consistent surface for SERS, while RealTime uses silver nanoparticles imbedded in a sol-gel that is coated on the inner surface of small vials. Both methods are optimized for a 785 nm excitation laser (minimal power).

Example 1

Figure 8:
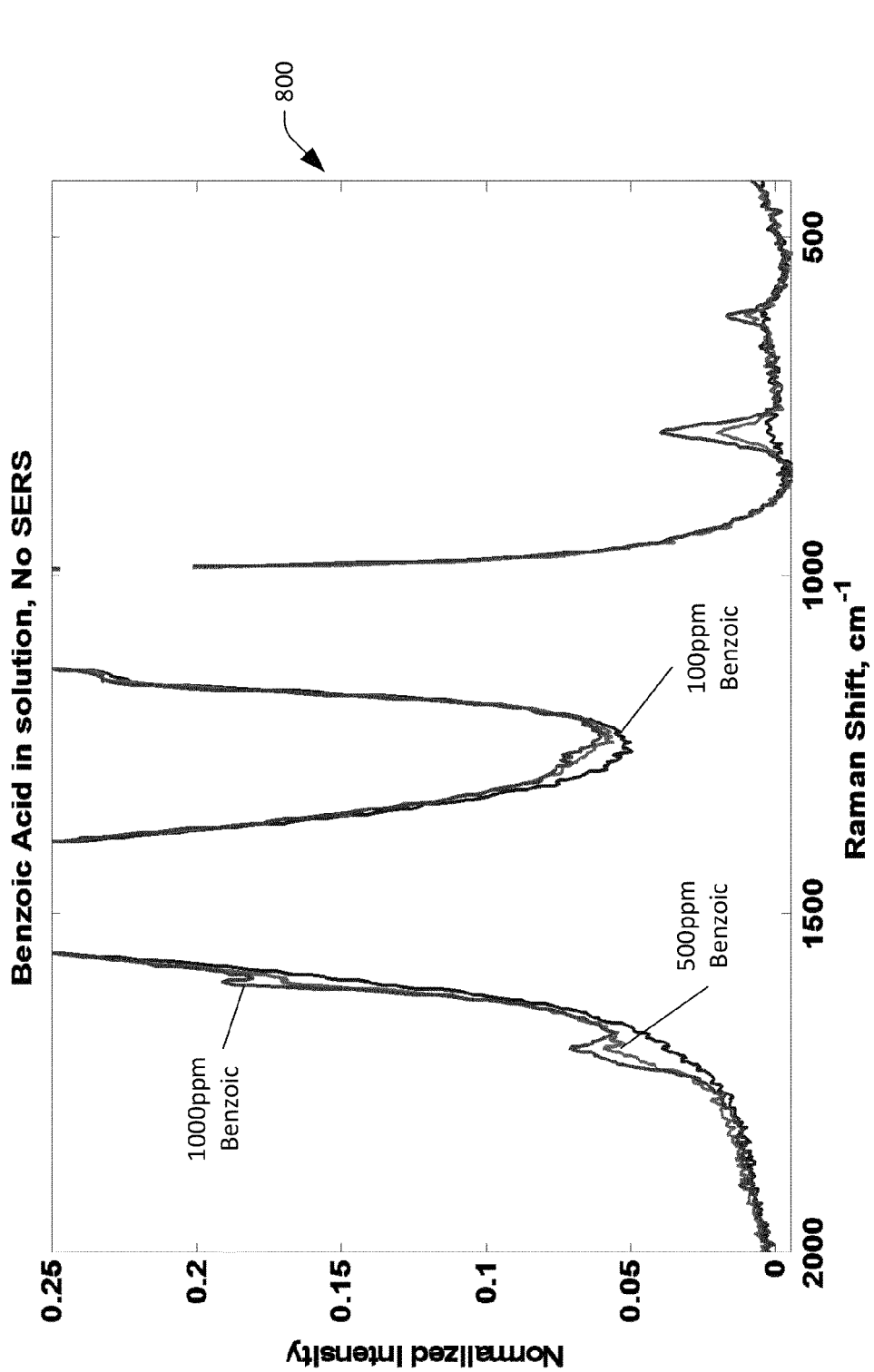
FIGS. 8-14 are graphs that illustrate various features pertaining to Raman spectroscopy.

Demonstration of SERS Enhancement Using a Portable Raman System and Commercial SERS Surfaces: Benzoic Acid The SERS effect and its detection limit were investigated using benzoic acid and the sol-gel coated (RealTime) vials. The 2-ml vials were coated with a sol-gel containing nanoparticles of silver. In solution, analytes diffuse through the matrix and interact with the silver particles, producing the SERS effect. Benzoic acid solutions, varying in concentration from 100 ppm to 10000 ppm, were prepared in methanol and analyzed using standard liquid sampling. These solutions were first sampled using standard vials and slides to provide a baseline measurement where the small benzoic acid bands can be seen on the large methanol bands in the graph 800 of FIG. 8. With no SERS enhancement, bands cannot be detected at 100 ppm benzoic acid.

Figure 9:
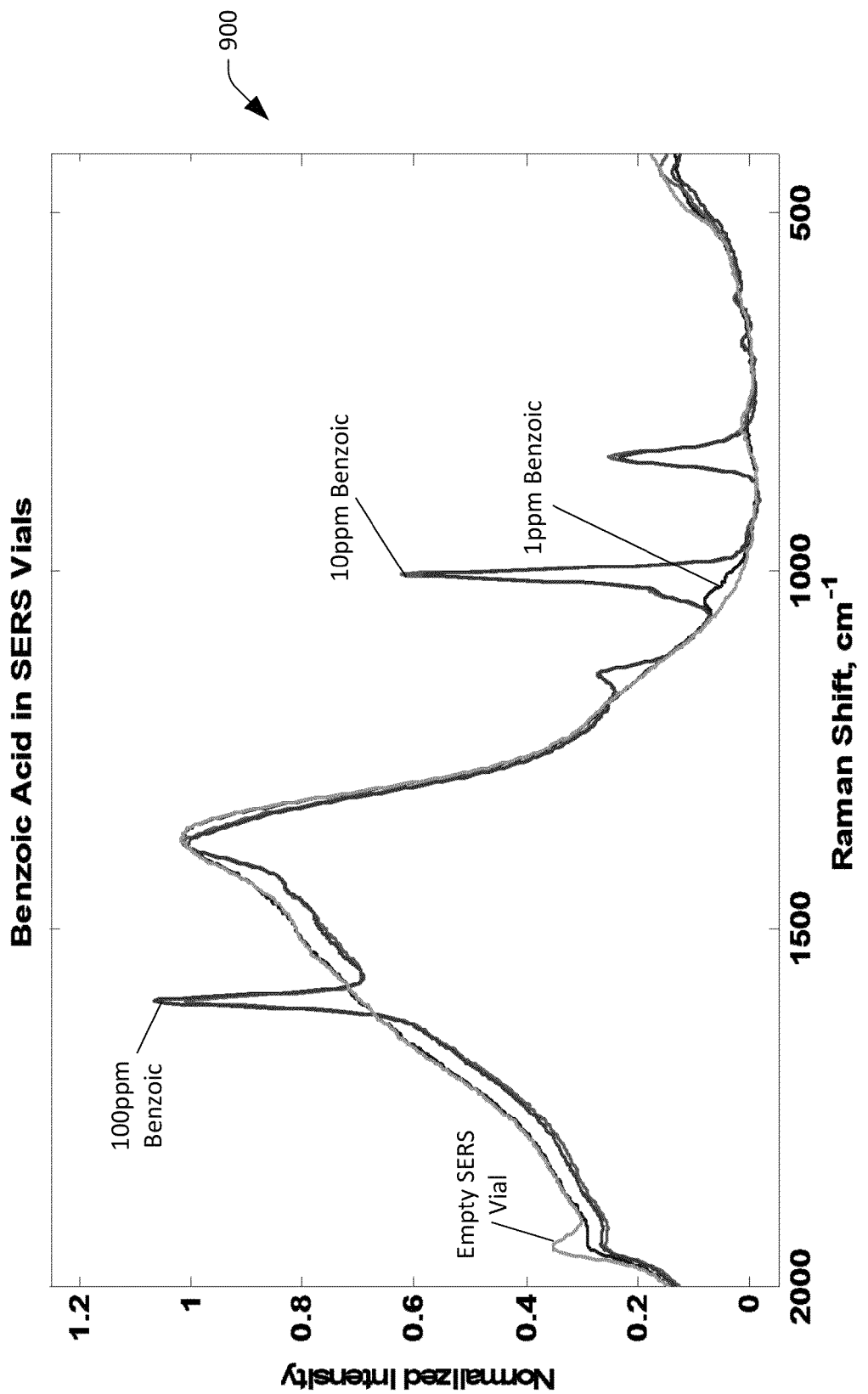

Placing these solutions in the RealTime SERS vials was shown to significantly increase the detection limit. SERS allows detection of at least a 10 ppm benzoic acid solution, as shown in graph 900 of FIG. 9. It can be noted that the bands of benzoic acid are at a slightly different location in SERS than they are in solution. This is because the plasmon interaction between the analyte and the SERS nanoparticles enhance different Raman transitions.

Figure 10:
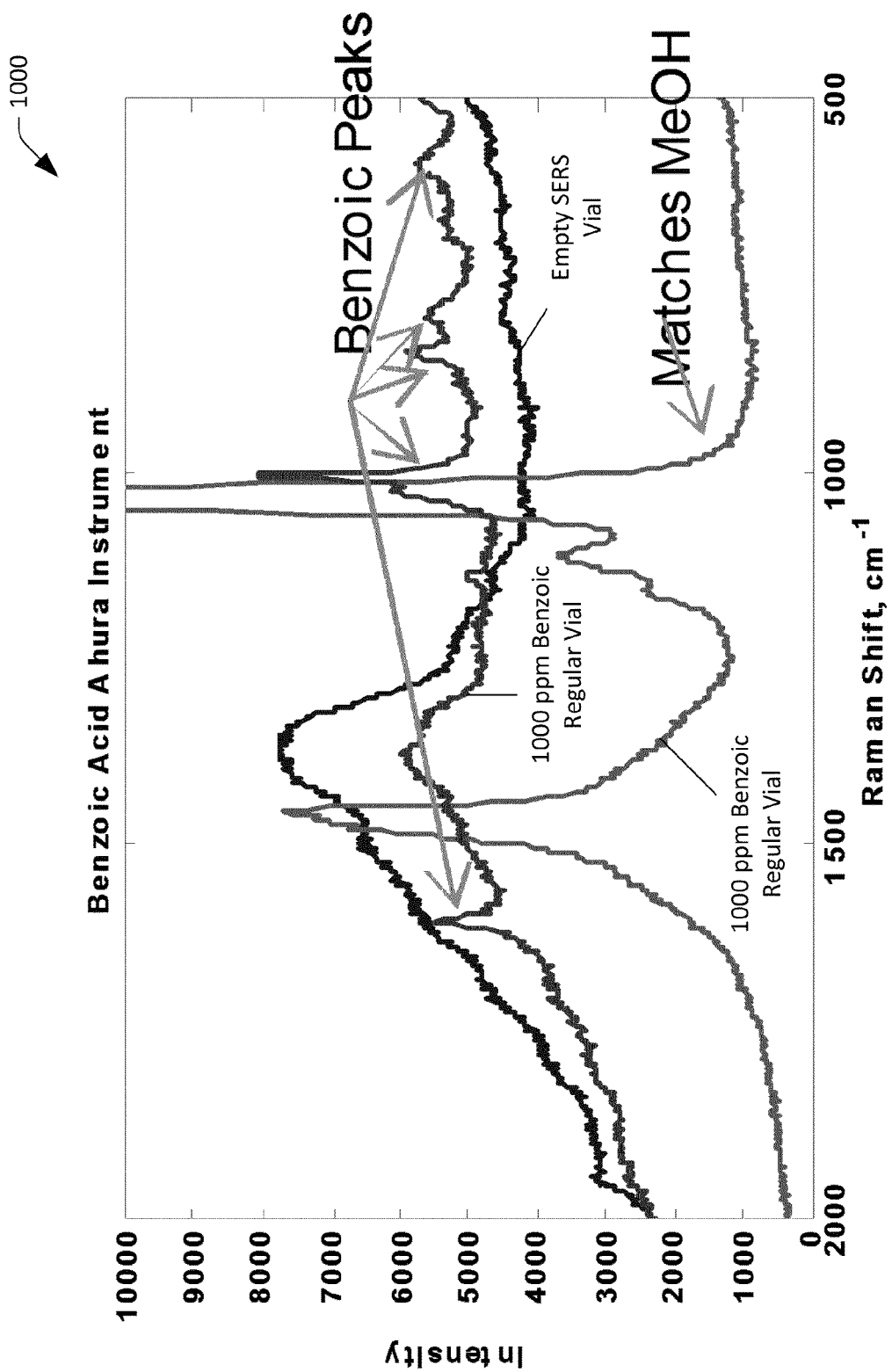

RealTime SERS vials containing the benzoic acid solutions were subsequently analyzed using the Thermo Scientific First Defender RM. Signals similar to those seen in FIG. 9 were obtained using the handheld system, and such signals are shown in graph 1000 of FIG. 10. As expected, these signals could not be matched to benzoic acid in the Ahura library due to the SERS shift of the bands.

Example 2

Demonstration of SERS Enhancement for an Explosive Precursor: Ammonium Nitrate

Figure 11:
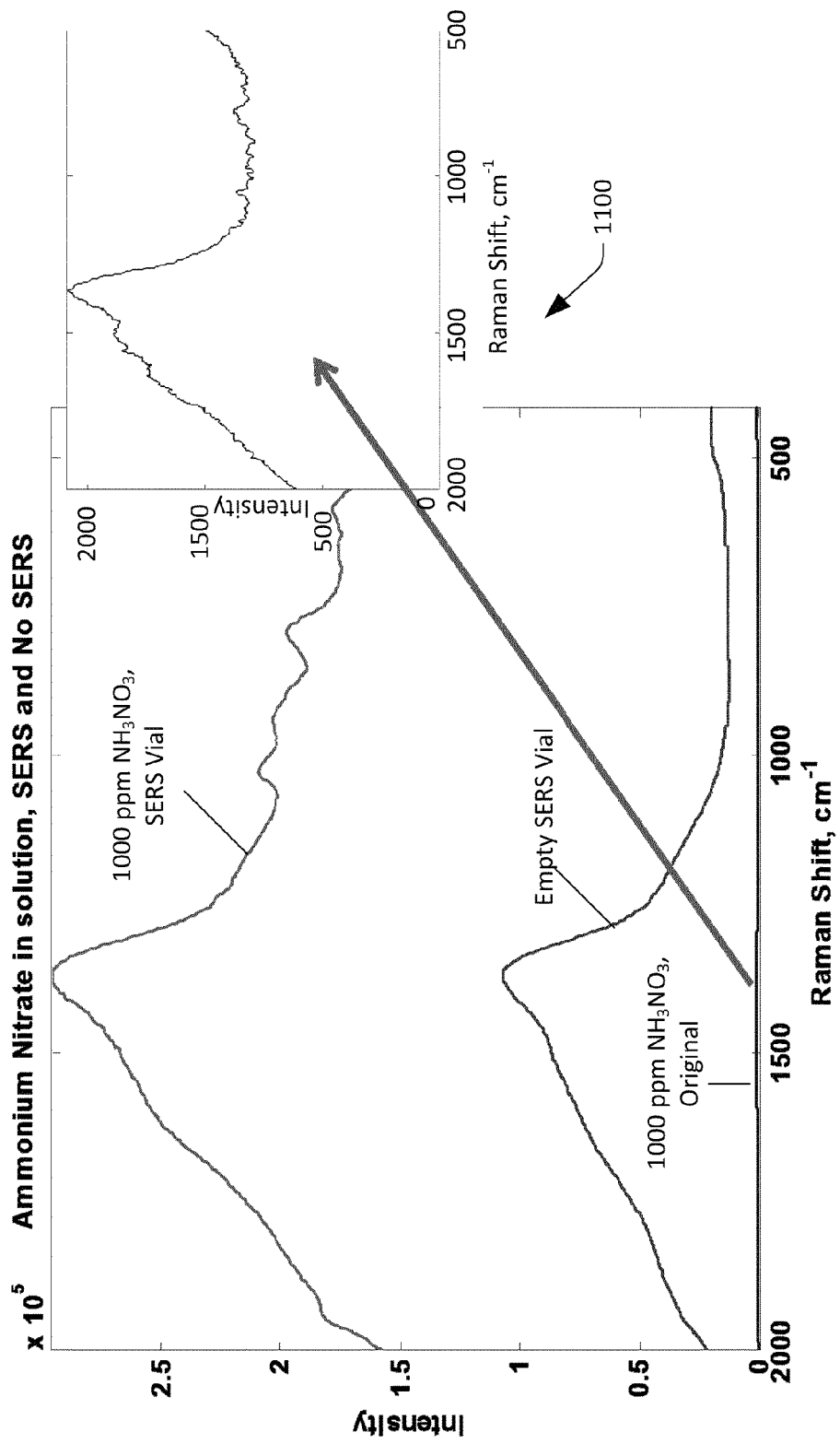

The enhancement of ammonium nitrate by SERS was investigated using SERS vials and SERS patterned substrates (Klarite slides). A 1000 ppm solution of ammonium nitrate was prepared in water. Raman data collected from the solution, are shown the graph 1100 of FIG. 11, along with the data collected from the solution placed in a SERS vial. All data were collected with the same instrument parameters (dwell time, laser power, etc.). Small peaks are barely visible in the original spectral data, when expanded (shown in window of FIG. 11). When placed in the SERS vial, ammonium nitrate peaks are readily detectable, indicating SERS enhancement.

Figure 12:
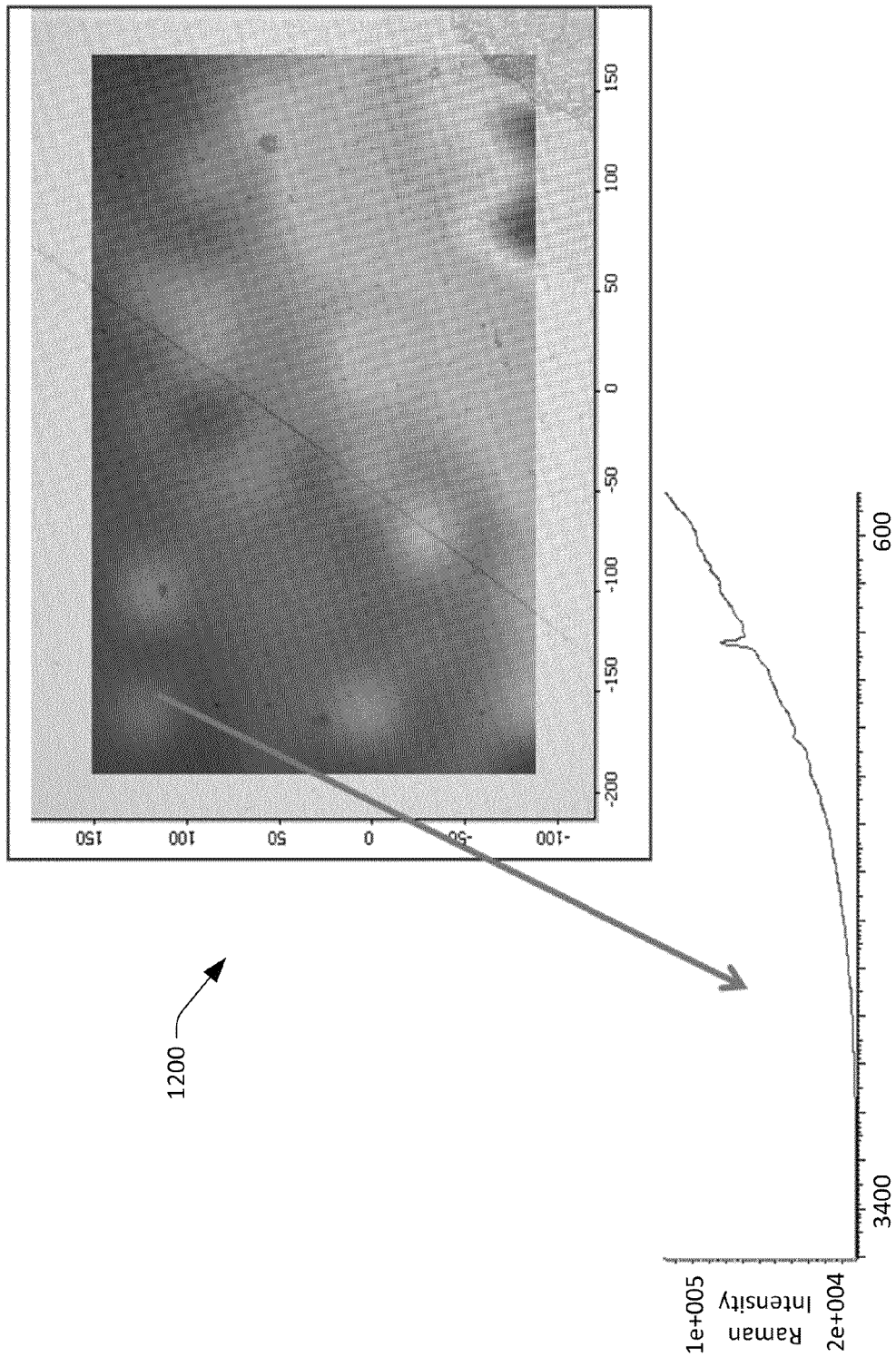

The 1000 ppm ammonium nitrate solution was spotted onto a Klarite slide. Maps of the spots were collected in order to discern concentration variation. A color intensity map of the 1052 $cm^{-1}$ nitrate peak is shown overlaid on the visible image of the slide in the plot 1200 of FIG. 12. Within the visible image, crystal formation can be clearly seen in the lower right corner, where, as expected, nitrate concentration is high. However, significant signal is seen far from the crystal, where solution had diffused (lower left graph, extracted from upper right corner of map), indicating SERS enhancement is likely occurring.

Both the vials and the patterned slides were used to show an enhancement of an ammonium nitrate signal (1000 ppm). The enhancement seen with the vials was slight, but significant compared to no enhancement. The patterned slide provided a significant enhancement of the Raman signal, over that seen in the vials and unenhanced solution.

Example 3

Demonstration of SERS Enhancement for an Explosive Compound: Trinitrotoluene (TNT)

The enhancement of TNT by SERS was investigated using SERS vials and SERS patterned substrates (Klarite slides). A 10,000 ppm solution of TNT was prepared in acetone. TNT could not be detected at a 10,000 ppm level with or without SERS enhancement using the RealTime vials or the Klarite patterned surface (unless visible crystals were found on the surface). Direct application of TNT by volatizing small amounts of TNT (1 mg or less) in the presence of the patterned surface also failed to result in a measureable TNT signal.

Figure 13:
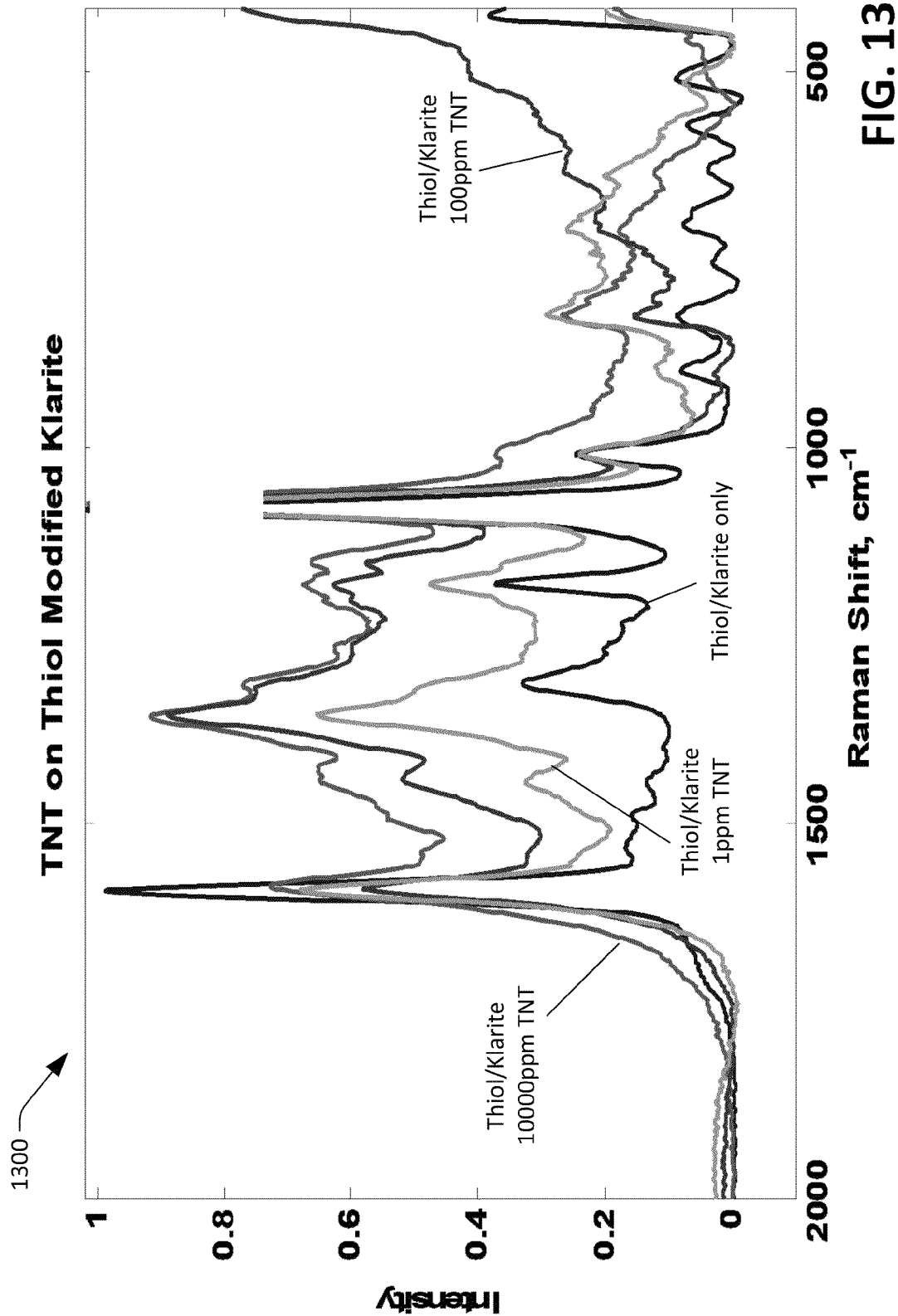

Previous studies have indicated surfaces for SERS detection of nitro-containing explosives will likely have to be functionalized in order to provide significant signal enhancement. The SERS surfaces were functionalized using thiol chemistry. Using a standard procedure, methylthiocarbanilide was attached to the Klarite surface. The altered plates were subsequently exposed to various concentrations of TNT in acetone solution and TNT vapor. For the liquid samples, a clear differentiation can be seen between those exposed to TNT and the thiol/Klarite slides (see graph 1300 of FIG. 13). TNT was readily detected at the 100 ppm level on the modified surfaces.

Figure 14:
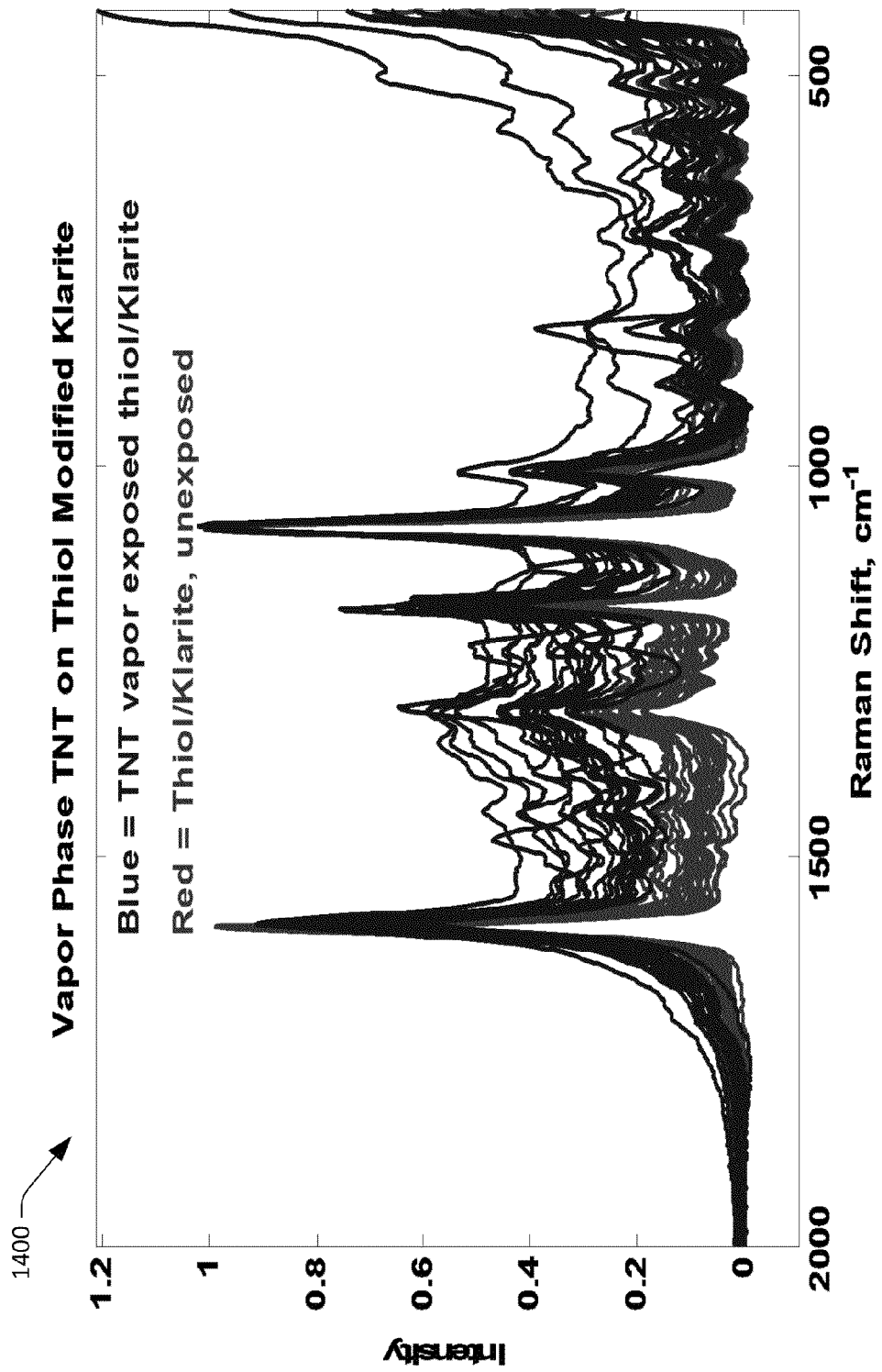

For the vapor-phase experiment, a thiol-modified Klarite slide was placed in a closed petri dish, containing 1 mg TNT. The petri dish was placed on a hot plate set at 50° C. The exposed plate was analyzed several days later. Results are shown in the graph 1400 of FIG. 14. Variations are notable in the spectra from the TNT exposed thiol/Klarite.

All patents, patent applications, publications, technical and/or scholarly articles, and other references cited or referred to herein are in their entirety incorporated herein by reference to the extent allowed by law. The discussion of those references is intended merely to summarize the assertions made therein. No admission is made that any such patents, patent applications, publications or references, or any portion thereof, are relevant, material, or prior art. The right to challenge the accuracy and pertinence of any assertion of such patents, patent applications, publications, and other references as relevant, material, or prior art is specifically reserved.

In the description above, for the purposes of explanation, numerous specific details have been set forth in order to provide a thorough understanding of the embodiments. It will be apparent however, to one skilled in the art, that one or more other embodiments may be practiced without some of these specific details. The particular embodiments described are not provided to limit the invention but to illustrate it. The scope of the invention is not to be determined by the specific examples provided above but only by the claims below. In other instances, well-known structures, devices, and operations have been shown in block diagram form or without detail in order to avoid obscuring the understanding of the description. Where considered appropriate, reference numerals or terminal portions of reference numerals have been repeated among the figures to indicate corresponding or analogous elements, which may optionally have similar characteristics.

It should also be appreciated that reference throughout this specification to "one embodiment", "an embodiment", "one or more embodiments", or "different embodiments", for example, means that a particular feature may be included in the practice of the invention. Similarly, it should be appreciated that in the description various features are sometimes grouped together in a single embodiment, figure, or description thereof for the purpose of streamlining the disclosure and aiding in the understanding of various inventive aspects. This method of disclosure, however, is not to be interpreted as reflecting an intention that the invention requires more features than are expressly recited in each claim. Rather, as the following claims reflect, inventive aspects may lie in less than all features of a single disclosed embodiment. Thus, the claims following the Detailed Description are hereby expressly incorporated into this Detailed Description, with each claim standing on its own as a separate embodiment of the invention.

What is claimed is:

1. An apparatus that facilitates performance of trace detection of at least one analyte, the apparatus comprising:
    a surface enhanced Raman spectroscopy (SERS) insert, the SERS insert comprises:
        a proximal end;
        a distal end;
        a plurality of passageways that extend laterally through the SERS insert from the proximal end to the distal end; and
        a plurality of thiol modified SERS surfaces that are respectively positioned in the passageways, each of the thiol modified SERS surfaces is configured to attract molecules of the at least one analyte, the SERS insert configured for insertion into a handheld Raman spectroscopy system.

2. The apparatus of claim 1, wherein a first thiol modified SERS surface is positioned in a first passageway and a second thiol modified SERS surface is positioned in a second passageway, the first thiol modified SERS surface configured to attract molecules of a first analyte, and the second thiol modified SERS surface configured to attract molecules of a second analyte.

3. The apparatus of claim 1, wherein the SERS insert is composed of a transparent material.

4. The apparatus of claim 1, wherein a number of passageways in the plurality of passageways is between two passageways and four passageways.

5. The apparatus of claim 1, the SERS insert being shaped as a cylinder.

6. The apparatus of claim 5, each of the passageways extending through the thiol modified SERS surface in parallel with one another and further in parallel with a central axis of the cylinder, each of the passageways at least partially defined by a respective planar inner surface and an outer surface, the inner surface located between the central axis and the outer service, the thiol modified SERS surface positioned on the planar inner surface.

7. The apparatus of claim 1, further comprising:
    a pre-concentrator that is in fluid communication with the SERS insert; and
    an analysis pump that is in fluid communication with the SERS insert, the analysis pump, when activated, configured to cause a concentrated sample to flow from the pre-concentrator and through at least one passageway in the plurality of passageways.

8. The apparatus of claim 7, wherein the pre-concentrator comprises a chamber that includes a sorbent material, the apparatus further comprising:
    a heater that is configured to heat the sorbent material in the chamber to a predefined temperature, the predefined temperature based upon the analyte.

9. The apparatus of claim 7, further comprising:
    a sample pump that is in fluid communication with the pre-concentrator, wherein the sample pump, when activated, is configured to direct air through the pre-concentrator.

10. The apparatus of claim 9, wherein the sample pump is configured to direct the air at a first flow rate, the analysis pump is configured to direct the concentrated sample at a second flow rate, the first flow rate being greater than the second flow rate.

11. An apparatus that facilitates trace detection of an analyte, the apparatus comprising: a pre-concentrator that is configured to generate a concentrated sample, wherein the pre-concentrator comprises: a sorbent material that is configured to absorb or adsorb molecules of the analyte, and a heater that is configured to heat the sorbent material to desorb the molecules from the material, the heater configured to heat the sorbent material to different temperatures depending upon a type of the analyte; and a SERS insert that comprises a SERS surface, the SERS surface in fluid communication with the pre-concentrator, the SERS surface configured to adsorb molecules of the analyte as the gas is directed over the SERS surface, wherein the SERS insert comprises: a plurality of passageways that extend in parallel with the axis of the SERS insert and through the SERS insert; and plurality of SERS surfaces respectively positioned in the passageways of the SERS insert, each SERS surface being configured to attract molecules of a respective analyte.

12. The apparatus of claim 11, the SERS insert being shaped as a cylinder and having a passageway that extends in parallel with an axis of the SERS insert and through the SERS insert, the SERS surface positioned in the passageway.

13. The apparatus of claim 12, wherein the SERS insert has a proximal end and a distal end, the SERS surface positionally biased towards the proximal end of the SERS insert.

14. The apparatus of claim 11, wherein the SERS surfaces is configured differently to attract different analytes.

* * * * *